United States Patent
Duplan et al.

(10) Patent No.: US 7,579,513 B2
(45) Date of Patent: Aug. 25, 2009

(54) METHOD FOR THE DIRECT CONVERSION OF A CHARGE CONTAINING OLEFINS COMPRISING A MINIMUM OF FOUR OR FIVE CARBON ATOMS, FOR PRODUCING PROPYLENE

(75) Inventors: Jean Luc Duplan, Irigny (FR); Sylvie Lacombe, St. Genis Laval (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 171 days.

(21) Appl. No.: 10/572,566

(22) PCT Filed: Sep. 2, 2004

(86) PCT No.: PCT/FR2004/002235

§ 371 (c)(1),
(2), (4) Date: Nov. 6, 2006

(87) PCT Pub. No.: WO2005/028594

PCT Pub. Date: Mar. 31, 2005

(65) Prior Publication Data

US 2007/0167662 A1    Jul. 19, 2007

(30) Foreign Application Priority Data

Sep. 19, 2003    (FR) .................................... 03 11031

(51) Int. Cl.
*C07C 4/02*    (2006.01)
*C10G 11/05*    (2006.01)

(52) U.S. Cl. ...................... 585/653; 585/651; 208/113; 208/118; 208/120.01

(58) Field of Classification Search ......... 585/651–653; 208/113, 118, 120.01
See application file for complete search history.

(56) References Cited

U.S. PATENT DOCUMENTS

| | | | |
|---|---|---|---|
| 6,093,867 A * | 7/2000 | Ladwig et al. | 585/648 |
| 6,222,087 B1 | 4/2001 | Ware et al. | |
| 7,375,257 B2 * | 5/2008 | Dath et al. | 585/653 |
| 2003/0139636 A1 | 7/2003 | Martens et al. | |

FOREIGN PATENT DOCUMENTS

| | | | |
|---|---|---|---|
| EP | 0921179 A1 | | 6/1999 |
| EP | 1195424 | * | 4/2002 |
| EP | 1195424 A1 | | 4/2002 |
| WO | 01/90034 A1 | | 11/2001 |

OTHER PUBLICATIONS

Written Opinion for PCT/2004/002235 dated Sep. 2, 2004 (6 pages).

* cited by examiner

*Primary Examiner*—In Suk Bullock
(74) *Attorney, Agent, or Firm*—Millen, White, Zelano, Branigan, P.C.

(57) ABSTRACT

The invention concerns a process for producing propylene, especially from a light steam cracking and/or catalytic cracking cut, preferably comprising both butenes and pentenes, said process comprising a step for moving bed catalytic cracking with a catalyst regeneration loop. The catalyst comprises at least one zeolite with a zeolitic composition with a Si/Al ratio which is preferably less than 130.

The invention can produce a high conversion with a good yield of propylene at a high space velocity, meaning that the volume of catalyst can be reduced.

16 Claims, No Drawings

METHOD FOR THE DIRECT CONVERSION OF A CHARGE CONTAINING OLEFINS COMPRISING A MINIMUM OF FOUR OR FIVE CARBON ATOMS, FOR PRODUCING PROPYLENE

FIELD OF THE INVENTION

The invention concerns a process for at least partially converting, into propylene, a hydrocarbon feed comprising olefins with a carbon number of 4 or more, for example a C4 and/or C5 cut from steam cracking or FCC. The term Cn designates a hydrocarbon cut essentially containing n carbon atoms, and the term FCC, the abbreviation for "fluid catalytic cracking", signifies fluidized (bed) catalytic cracking. In general, and in the present invention, the term "FCC" designates the conventional process used in the refineries for catalytically cracking heavy oil fractions, using a feed boiling principally above about 350° C. (at least 50% by weight, generally at least 70% by weight and usually 100% by weight of the feed boiling above 350° C.), for example a vacuum distillate, or possibly deasphalted oil or atmospheric residue. By extension, it also designates similar fluidized bed processes operating at higher temperatures, such as about 580° C. to 700° C. at the reactor outlet, and/or using catalysts comprising high reactivity zeolites such as ZSM-5, to obtain high yield conversion of the feed and an increased production of light olefins.

Said olefinic C4/C5 cuts are available in large quantities, often to excess, in oil refineries and steam cracking facilities. Recycling them is a problem, however:

recycling them to the steam cracking step has disadvantages (the light olefin yields are lower than with paraffinic cuts and they have a relatively greater tendency to form coke);

recycling them to the FCC step cannot really be envisaged as they are only slightly reactive under FCC conditions, which are adapted to the vacuum distillate feed. Recycling them to the FCC step would thus necessitate the use of much more severe conditions or specific catalysts, which would substantially modify the operation of the FCC step. This could not be adapted to cracking both the vacuum distillate and the C4/C5 cuts.

The feed for the process of the invention may also comprise C4/C5 fractions, or wider fractions from a chamber or fluidized bed cokefaction unit, or from visbreaking, or from the Fischer-Tropsch synthesis. The feed may also comprise fractions of a steam cracking gasoline or from a FCC gasoline, or from another olefinic gasoline. (The term "gasoline" generally means a hydrocarbon cut mostly derived from at least one conversion or synthesis unit (such as FCC, visbreaking, cokefaction, a Fischer-Tropsch unit, etc) and in which the majority and typically at least 90% by weight of this cut is constituted by hydrocarbons containing at least 5 carbon atoms and a boiling point of 220° C. or less).

The olefinic cut constituting the feed for the process of the invention generally comprises olefins containing 2 to 12 carbon atoms. It is preferably selected from the feeds defined above, or comprises a mixture of the feeds defined above. A typical feed usually comprises butenes and/or pentenes in a substantial or major quantity, and is typically constituted by an olefinic C4/C5 cut. It may also comprise ethylene, possibly small quantities of non-fractionated propylene, hexenes, olefins containing 7 to 10 carbon atoms. Usually, the feed is not purely olefinic, but also comprises paraffins (in particular n-butane and/or isobutane, pentanes, and sometimes aromatic compounds, in particular benzene and/or toluene, and/or xylenes. It may comprise isobutene and/or isoamylenes.

The feed also often comprises highly unsaturated compounds: dienes (diolefins) containing 4, 5 carbon atoms, especially (in particular butadiene), and small quantities of acetylenic compounds containing 2 to 10 carbon atoms.

The feed is thus typically a light olefinic feed, the distillation end point of which (using the TBP method which is well known to the skilled person) or at least the point at which 90% by weight of the feed has been distilled, is very generally less than 320° C., and generally less than 250° C.

The process for converting a light olefinic feed into a cut comprising propylene of the present invention employs catalytic reactions that can directly convert these light olefins into propylene, i.e. without a preliminary olefin oligomerization step.

The unit for carrying out the process of the invention is preferably installed close to or at a refining site (oil refinery) or a petrochemicals site (steam cracker).

PRIOR ART

A known process for direct propylene production beyond conventional production processes, namely FCC and steam cracking (where propylene is co-produced with other products such as gasoline or ethylene), is the metathesis process which converts an ethylene+n-butene mixture into propylene. That process is described in French patent FR-A-2 608 595.

One advantage of the process of this invention over metathesis is to produce propylene from the set of olefinic compounds from C4, C5 cuts and optionally from hydrocarbon cuts with a higher number of carbon atoms, in particular gasoline, and of not requiring a massive consumption of ethylene, which is an expensive substance. If it is applied to a steam cracking site, the process of the invention not only does not use ethylene as the feed, but it can also co-produce ethylene with propylene. Ethylene co-production is typically lower than that of propylene, which means that the propylene to ethylene ration of the steam cracker can be increased.

Further, if applied to an oil refinery, the process of the invention can, in contrast, upgrade (over and above C4/C5 cuts) the ethylene which, because it is present in relatively limited amounts, as is often the case in a refinery, is difficult to upgrade.

Other processes for producing propylene from olefinic C4 and C5 cuts in a single chemical conversion step (i.e. without prior oligomerization) are also known:

A further process for producing propylene in one step from light olefins is a variation of the FCC process using a catalyst comprising a ZSM-5 zeolite. That process is described in International patent application WO-A-01/04237 and in the article "Maximizing refinery propylene production using ZSM-5 technology", in the review "Hart's Fuel Technology and Management", May 1998. The typical operating conditions for this process are a temperature of close to 600° C., and a pressure of 0.1 to 0.2 MPa.

Under these conditions, the propylene yield is about 30% and may increase to 50% with a recycle of the unreacted C4 and C5 cuts.

One disadvantage of that process is that fluidized bed technology is relatively expensive from the point of view of investment and the process is quite difficult to control. It also results in substantial losses of catalyst by wear.

In the family of once-through processes (with no prior oligomerization of C4/C5 fractions), it is also possible to cite a process a description of which can be found in the article "Production propylene from low valued olefins" in the review "Hydrocarbon Engineering", May 1999. It is a fixed bed process the catalyst of which is a ZSM-5 type zeolite acting in the presence of steam. The temperature is close to 500° C. and the pressure is in the range 0.1 to 0.2 MPa. The stated cycle time is of the order of 1000 hours. The catalyst is regenerated in situ and the overall service life, i.e. the period during which it is used in the reactor without being completely renewed, is about 15 months. The stated propylene yield is about 40% and could rise to 60% with a recycle of unreacted C4 and C5 cuts. That process can obtain a relatively high propylene yield. However, it requires the use of large quantities of steam.

It is also possible to cite a process described in EP-B1-0 109 059. It is a process using a zeolitic ZSM-5 or ZSM-11 type zeolitic catalyst having particular characteristics, used at a high space velocity. Test results, very probably of short duration and in a fixed bed (micro-reactor) are indicated.

It is also possible to cite a process described in International patent application WO-A-99/29805, and in European patent applications or patents EP-A-0 921 181 and EP-A-0 921 179. The process uses a MFI type zeolitic catalyst having a high Si/Al ratio (180 to 1000) to limit the hydrogen transfer reactions responsible for the production dienes and aromatics. The temperature is close to 550° C., the pressure is close to 0.1 MPa and the space velocity is in the range $10\ h^{-1}$ to $30\ h^{-1}$. That process mentions the possibility of fixed, moving or fluidized bed reactors. It presents various experimental test results, including long term tests, and recommends the use of a fixed bed reactor, or more exactly two swing fixed-bed reactors one of which is in operation and the other of which is in regeneration. The catalyst used comprises a MFI type zeolite the Si/Al ratio of which (silicon/aluminium atomic ratio) is expressly greater than or equal to 180, preferably a ZSM-5 zeolite with a Si/Al ratio in the range 300 to 1000.

The use of dealuminated zeolites with such a high Si/Al ratio is recommended and claimed both to limit hydrogen transfer reactions and help with catalyst activity stability.

Finally, the process described in European patent application EP-A1-1 195 424 may be cited. It is a process which also uses an MFI type zeolitic catalyst having a Si/Al ratio of 180 to 1000, or a MEL type zeolitic catalyst having an Si/Al ratio of 150 to 800, these high Si/Al ratios also being used to limit the hydrogen transfer reactions responsible for the production of dienes and aromatics. The temperature is in the range 500° C. to 600° C., the partial pressure of olefins is in the range 0.01 to 0.2 MPa, and the space velocity is in the range $5\ h^{-1}$ to $30\ h^{-1}$. This process, which represents the prior art which is closest to the invention, uses a moving bed with intermittent removal of catalyst which is regenerated and recycled.

DETAILED DESCRIPTION OF THE INVENTION

The Applicant has discovered that it is possible to carry out a process having advantages over the prior art. Compared with (swing) fixed bed processes of the prior art, the process of the invention can provide continuity of operation of the cracking unit (typically, the same reactor can operate for more than a year, or even longer, without stopping the reactor). Compared with moving bed processes, in particular the process described in European patent EP-A1-1 195 424, the process of the invention can also attain a high conversion and yield, but with a smaller catalytic volume mainly thanks to the use of a suitable catalyst and a typically increased space velocity.

The technology of the chemical reactor operating in moving granular catalytic bed mode with a catalyst regeneration loop is a technology which is well known in the oil and petrochemicals industry and used in many processes, for example in continuous hydrocarbon catalytic reforming processes. Typically, one or more radial reactors are used with continuous or generally intermittent removal of catalyst from the lower portion of the reactor. As an example, a lift pot can be used to collect the catalyst, then transfer it by pneumatic transport, for example using a stream of nitrogen, to the next reactor or to the regeneration zone in which the catalyst is regenerated by one or more operations comprising at least controlled oxidation of carbonaceous deposits or of coke by air or a gas containing oxygen, for example nitrogen supplemented with air. The regenerated catalyst is then transferred, by gravity flow or by pneumatic transport, to the upper portion of the reactor or to another reactor. The regeneration zone may also operate as a moving bed, at a pressure which is generally close to the mean pressure of the process and at a temperature which is generally in the range 400° C. to 650° C. When several reactors are used, the catalyst may move as a counter current as a whole, or as a co-current together with the feed. To obtain other details regarding moving bed processes, it may be referred to United States patents U.S. Pat. Nos. 3,838,039, 5,336,829, 5,849,976 and to European patent application EP-A1 1 195 424.

More precisely, the invention concerns a process for direct conversion (i.e. without prior oligomerization of olefins) by catalytic cracking of a light olefinic hydrocarbon feed comprising at least 80% by weight of hydrocarbons containing at most 12 carbon atoms for the production of propylene, said process comprising direct cracking of the feed on a supported catalyst comprising at least one zeolite comprising silicon and aluminium and having form selectivity, from the group constituted by zeolites with one of the following structure types: MEL, MFI, NES, EUO, FER, CHA, MFS, MWW, and from the following zeolites: NU-85, NU-86, NU-88 and IM-5, comprising circulating the feed at a temperature in the range about 480° C. to 620° C. in at least one reactor on a granular moving bed of said catalyst, extracting from the lower portion of the reactor, continuously or discontinuously, a flow of catalyst comprising a carbonaceous deposit, transferring said catalyst to a regeneration zone where it undergoes at least one controlled oxidation step then, downstream of the regeneration zone, re-introducing the catalyst comprising a reduced amount of carbonaceous deposit (compared with the extracted catalyst) directly or indirectly into the upper portion of said reactor.

The catalysts which can be used in the invention are such that the zeolites of the group cited above may, in accordance with various variations of the invention, have a Si/Al atomic ratio which can vary widely. As an example, they have a Si/Al ratio typically in the range 20 to 1500. However, in one of the preferred variations of the invention, the zeolites of said group have a Si/Al ratio of less than 160, for example one or more zeolites of the sub-group MFI (for example ZSM-5), with a Si/Al ratio of less than 160, in particular in the range 30 to 160.

In general, one or more zeolites from the (largest) group cited above may advantageously be used, which has a Si/Al ratio of less than 130, for example in the range 40 to 130, or in the range 60 to 120, and in particular one or more zeolites of the sub-group constituted by zeolites with structure type MFI, MEL, CHA, with such Si/Al ratios.

Typically, at least 80% by weight of the feed derives directly from one or more hydrocarbon cracking units, for example from FCC, steam cracking, visbreaking and cokefaction group units.

The feed may also comprise fractions deriving directly from one or more Fischer-Tropsch synthesis units, for example at least 10% by weight of said fractions.

Preferably, the zeolite or zeolites of said group belong to the sub-group constituted by zeolites with structure type MEL, MFI and CHA, or to the sub group of zeolites with structure type MFI. In particular, a ZSM-5 zeolite may be used.

Typically, the process can use an overall space velocity HSV (with respect to the totality of the reaction zones or reactors) which is generally in the range 7 to 100, preferably in the range 13 to 80, or even in the range 33 to 60, which can further reduce the catalytic volume. In a preferred variation of the invention, a catalyst which is more active than those of the prior art described in EP-A-0 921 181 and in EP-A1-1 195 424 is used. Advantageously, a relatively low Si/Al ratio is used, with an increased hourly space velocity, limiting the contact time for which the cracking reaction forming propylene approaches thermodynamic equilibrium without causing hydrogen transfer reactions to progress. For a constant catalyst flow rate, the high hourly space velocity can also reduce the residence time in the reactor. The use of a lower Si/Al ratio and thus increased activity catalyst jointly with an increased HSV can reduce the residence time of the catalyst in the total reaction zone, and thus can counteract the increase in the cokefaction rate of the catalyst due to increased hydrogen transfer resulting from the lower Si/Al ratio. A new equilibrium of the operating variables is then reached with a reaction volume which can be substantially reduced with respect to the prior art.

In a preferred variation of the invention, which can be used with the low Si/Al ratios cited above, but also with very high Si/Al ratios, for example between 130 and 1200 or even higher, a moving bed with an atypical circulation rate is used, in particular with residence times in the reactor (or in the total reaction zone, if several reaction zones or several reactors are used) which may be in the range 1 to 40 hours, and preferably in the range 2 to 18 hours. These values are very low with respect to conventional moving beds used, for example, for regenerative catalytic reforming where overall residence times (for the whole set of the reactors) are typically 2 to 3 days. They may be obtained by using high HSVs and by maintaining high degrees of removal of coked catalyst sent to the regeneration zone. Using high withdrawal rates can result in a supplemental reduction in the residence time of the catalyst in the total reaction zone, and thus further counteract the increase in the catalyst cokefaction rate due to increased hydrogen transfer resulting from a Si/Al ratio which is often low.

To further reduce hydrogen transfer, in a preferred variation of the invention, and regardless of the Si/Al ratio, the feed may advantageously be diluted, in particular in an amount of 10% to 70% molar of diluent, with a mixture of hydrogen and methane, in particular by such a mixture from the effluent fractionation train of a steam cracker. This is advantageous if the steam cracker is located at the same site as the moving bed catalytic cracking unit of the invention, which cracks a portion of the light fractions (C4/C5 in particular) produced by the steam cracker. It is also possible to use steam (alone or with the mixture of hydrogen and methane) to reduce the partial pressure of the hydrocarbons.

In a preferred implementation of the process of the invention, the feed traverses 2 or 3 moving bed reaction zones in series with intermediate reheating between two successive zones. It is possible to use several reactors or several reaction zones in the same reactor. The space velocity HSV in each reaction zone may, for example, be in the range 14 to 160, in particular in the range 66 to 120. Optionally, it is possible to use a higher space velocity in the first reactor.

Before being introduced into the moving bed cracking unit, the feed may preferably undergo prior selective hydrogenation in a preliminary step to eliminate diolefins and other acetylenic impurities often present in the feed. These various highly unsaturated compounds contribute to a certain deactivation of the cracking catalyst and selective hydrogenation which can increase the quantity of convertible olefins.

The catalytic cracking effluent typically undergoes a fractionation step usually comprising compression of the gas and one or more distillation steps to separate the effluents and produce a c3 cut which is rich in propylene, or substantially pure propylene.

If the catalytic cracking unit of the process of the invention is located on the same site as the steam cracking unit, or a FCC unit, the catalytic cracking effluents may be combined with those from steam cracking or FCC, to be fractionated together. Because of the low reactivity of paraffins in catalytic cracking, this may increase the quantity of paraffins which are unreacted in the recovered olefinic fraction, principally composed of steam cracking effluents, which is sent to the catalytic cracking step of the invention. To avoid excessive build up of this reserve of paraffins, part of the olefinic feed may be eliminated by a purge, for example of the C5/C6 cut, this purge not being recycled to the catalytic cracking of the invention. The purge may be re-cracked by recycling to the steam cracking furnaces.

It is also possible to treat and separate the moving bed catalytic cracking effluents separately from those from steam cracking, or FCC.

We shall now describe, in further detail, the particular conditions of the various reaction steps of the process of the invention, in a variation comprising selective hydrogenation then moving bed catalytic cracking, integrated into the same site, the feed used being a light C4 and C5 hydrocarbon cut principally containing butenes, pentenes, butanes, pentanes and in some cases butadiene and pentadiene in variable quantities.

1) Selective hydrogenation preferred optional step):

The light cut typically derives from a FCC catalytic cracker and/or a steam cracker. The diene and acetylenic contents are high when this cut derives from a steam cracker; this is why the step for selective hydrogenation of dienes and acetylenics to olefins is virtually indispensable in this case. It is also preferable in the majority of cases as it reduces coking of the cracking catalyst and increases propylene conversion. However, the scope of the invention encompasses the possibility of such a selective hydrogenation step not being included in the process of the invention.

The principal aim of this first step is to transform the diolefins (or dienes) into mono-olefins. Mono-olefins are a source of reactive molecules in catalytic cracking. The second aim of this step is to eliminate traces of acetylenic hydrocarbons always present in these cuts and which are unwanted compounds for catalytic cracking, encouraging catalyst coking. These compounds are also transformed into mono-olefins.

When the proportion of diolefins in the cut is high, transformation may advantageously be carried out in two or three reactors in series to better control the hydrogenation selectivity. Frequently, the feed to be treated is diluted by recycling a certain flow of the effluent from said selective hydrogenation.

The residual diolefins+acetylenics content of the selective hydrogenation effluent is typically less than about 1000 ppm by weight, preferably less than about 100 ppm by weight and more preferably less than 20 ppm by weight. The residual acetylenics content may even be below 10 ppm or 5 ppm, or even less than 1 ppm by weight.

The quantity of hydrogen necessary for the set of reactions carried out in this step is generally adjusted as a function of the composition of the cut to advantageously have only a slight excess of hydrogen with respect to the stoichiometry.

In general, this selective hydrogenation step is carried out using a catalyst comprising at least one metal selected from the group formed by nickel, palladium and platinum deposited on a support comprising alumina, silica or silica-alumina. Preferably, a catalyst is used which comprises at least palladium or a palladium compound fixed on a refractory mineral support, for example on an alumina or a silica-alumina. The palladium content on the support may typically be 0.01% to 5% by weight, preferably 0.05% to 1% by weight. Various pre-treatment modes which are known to the skilled person may optionally be applied to these catalysts to improve their hydrogenation selectivity as regards mono-olefins.

The operating temperature of the selective hydrogenation step is generally in the range 0° C. to 200° C., the typical pressure is in the range 0.1 to 5 MPa, usually in the range 0.5 to 5 MPa, the hourly space velocity is typically in the range 0.5 to 20 m$^3$ per hour per m$^3$ of catalyst, usually in the range 0.5 to 5 m$^3$ per hour per m$^3$ of catalyst, and the molar H$_2$/(acetylenic+diolefinic compounds) ratio is generally in the range 0.5 to 5, preferably in the range 1 to 3.

In general, to carry out selective hydrogenation, a fixed bed reactor traversed in co-current mode downflow mode by the feed to be treated and hydrogen, or in downflow mode for the feed to be treated and in upflow mode for the hydrogen.

It is also possible to carry out one or more optional purification steps for the feed (for example desulphurization and/or drying and/or denitrogenation and/or deoxygenation) upstream of the catalytic cracking, if necessary, as a function of the feed and catalyst used.

The selective hydrogenation step is essential in the case of olefinic cuts from steam cracking (in particular C4/C5 cuts) because of their very high butadiene content.

It is also possible to extract isobutene before the moving bed catalytic cracking of the invention.

The isobutene may be extracted by extractive distillation, for example with a solvent which may be N-methyl pyrrolidone (NMP) or dimethylsulphoxide (DMSO) or an isomer thereof.

Extraction of isobutene and optionally of other branched olefins, in particular isoamylenes, may also comprise etherification of isobutene by an alcohol followed by distillation. Hydroisomerization may also be carried out with reactive distillation to separate the isobutene from the butene (1-butene being transformed into 2-butene which can be separated from the isobutene).

2) Catalytic cracking:

The feed fed to the moving bed catalytic cracking step typically contains 20% to 100% by weight, usually 25% to 60% by weight of olefins, in particular light olefins containing 4 and/or 5 carbon atoms.

Typically, the catalyst may comprise at least one zeolite having form selectivity, this zeolite comprising silicon and at least one element selected from the group formed by aluminium, iron, gallium phosphorus, boron and, preferably, aluminium. This zeolite having form selectivity may be one of the following structure types: MEL (for example ZSM-11), MFI (for example ZSM-5), NES, EUO, FER, CHA (for example SAPO-34), MFS, MWW or one of the following zeolites: NU-85, NU-86, NU-88 or IM5, which also have form selectivity.

One advantage of said zeolites having form selectivity is that it results in better propylene/isobutene selectivity (higher propylene/isobutene ratio in the cracking effluents).

It is also possible to use several zeolites having form selectivity, for example a MFI type zeolite (for example ZSM-5) associated with another zeolite having form selectivity, as cited above, or one of the types cited above.

The zeolite or zeolites having form selectivity of the group formed by one of the following structure types: MEL (for example ZSM-11), MFI (for example ZSM-5), NES, EUO, FER, CHA (for example SAPO-34), MFS, MWW or from one of the following zeolites: NU-85, NU-86, NU-88 or IM-5, may also be mixed with a zeolite having no form selectivity, such as a Y zeolite with structure type FAU.

Frequently, a catalyst is used comprising one or more zeolites having form selectivity, the proportion of zeolites having form selectivity being in the range 70% to 100% by weight, limits included, with respect to the total zeolite quantity. It is in particular possible to use a catalyst the proportion of zeolite having form selectivity of which is in the range 80% to 100% by weight with respect to the total quantity of zeolite(s), and even a catalyst the zeolite or zeolites of which all have form selectivity.

The zeolite or zeolites may be dispersed in a matrix based on silica, zirconia, alumina or silica alumina, the proportion of zeolite (and generally zeolite having form selectivity) usually being in the range 15% to 80% by weight, preferably in the range 30% to 75% by weight, for example in the range 40% to 75% by weight. The matrix is preferably selected to be slightly acidic or non acidic. In particular, a matrix with a reduced or zero alumina content may be used, for example silica and/or zirconia.

In accordance with the invention, the zeolite used (or zeolites used) having form selectivity preferably have a relatively low Si/Al ratio, for example less than 300 or even less than 130. The synthesis of zeolites is a field which is well known to the skilled person. Examples of synthesis are given, for example, in the following patents or patent applications: U.S. Pat. No. 3,702,886 (ZSM-5, Example 24), U.S. Pat. No. 3,709,979 (ZSM-11), FR-A-2 755 958 and EP-A2-0 463 768 (NU-86), EP-A-0 921 181 and EP-A-0 921 179 (ZSM-5), and EP-A1-1 195 424 (ZSM-5 and ZSM-11). Other information regarding zeolites can be obtained from the "Atlas of zeolite structure types" by Meier W M and Olsen D H, 1992, published by Butterworths, zeolites vol 2, No 15, June 1992, and regarding synthesis methods in "Synthesis of high silica aluminosilicate zeolites" by P A Jacobs and J A Martens, Studies in surface science and catalysis, vol 33, Elsevier, 1987.

Varying moderate or high Si/Al ratios may be obtained on manufacture of the zeolite or by subsequent dealumination and elimination of alumina. In particular, it is possible to use one of the commercial ZSM-5 zeolites: CBV 28014 (Si/Al ratio of 140), and CBV 1502 (Si/Al ratio of 75) from Zeolyst International, Valley Forge, Pa., 19482 USA, or ZSM-5 Pentasil with a Si/Al ratio of 125, from Sud-Chimie (Munich, Germany).

By way of example, it is also possible to use the following method for preparing a ZSM-5 zeolite with a Si/Al ratio of 120:

The composition of the gel used for the synthesis is defined in Table 1.

TABLE 1

| Composition of gel | |
|---|---|
| SiO$_2$ (mol) | 60 |
| Al$_2$O$_3$ (mol) | 0.3 |
| Na$_2$O (mol) | 10 |

TABLE 1-continued

| Composition of gel | |
|---|---|
| TPABr (mol) | 7 |
| H$_2$O (mol) | 2000 |

TPABr = tetrapropylammonium bromide.

A solution A was prepared composed of water, solid sodium hydroxide (Prolabo) and tetrapropylammonium bromide (Fluka). A solution B was prepared by adding aluminium hydroxide (Reheis Ireland) to solution A with stirring. It was mixed at temperature for about fifteen minutes. Silica (Ludox HS40, Dupont de Nemours) was then added, with stirring. It was mixed at ambient temperature until homogenization, i.e. for about one hour. The resulting mixture was reacted in an autoclave with stirring for 4 days at 175° C. under autogenous pressure. After cooling, the product was filtered and washed with demineralized water, then dried in a ventilated oven at 120° C. The solid was calcined at 550° C. in air for 5 h to eliminate the organic template. The solid obtained underwent three ion exchange steps in a 10N solution of NH$_4$NO$_3$ at about 100° C. for 4 hours for each exchange.

X ray diffraction analysis carried out on the product obtained showed that the product was constituted by well crystallized pure MFI zeolite. An elemental analysis by X ray fluorescence recorded a molar Si/Al ratio of 123. The sodium weight content with respect to the weight of dry MFI zeolite was 85 ppm.

The zeolite underwent steam treatment at 600° C. in 50% vol steam in nitrogen for 5 hours.

To manufacture the catalyst, conventional techniques could be used, for example mixing the zeolite with silica gel precursors and/or silica gels, then shaping into small beads by drop coagulation, drying then calcining the beads to obtain the final catalyst.

When starting from a zeolite with a Si/Al ratio lower than the desired value, to increase this ratio, it is possible to carry out dealumination followed by a treatment to eliminate amorphous alumina. The dealumination treatment, which can eliminate aluminium from the zeolitic structure, may be carried out in an atmosphere of steam at a pressure of 20 to 200 kPa, at a temperature in the range 500° C. to 800° C., and for a period in the range 1 to 200 hours. The treatment intensity (duration, temperature, or steam pressure) is adjusted as a function of the initial Si/Al ratio of the zeolite and of the final desired ratio. The amorphous alumina extracted from the zeolitic structure is then eliminated by subsequent extraction treatment with formation of a water soluble aluminium complex. Other elements may be found in the following patents or patent application for carrying out these treatments or for manufacturing cracking catalysts s: WO-A-99/29805, EP-A-0 921 181 and EP-A-0 921 179.

The catalyst is employed in a moving bed, in the form of beads (preferably) or extrudates with a diameter generally in the range 0.4 to 6 mm, preferably in the range 0.6 to 4 mm.

The regeneration phase typically comprises a phase for combustion of carbonaceous deposits formed on the catalyst, for example using a mixture of air/nitrogen or air depleted in oxygen (for example by recirculating effluent), or air, and may optionally comprise other phases for catalyst treatment and regeneration.

It is also possible, according to preferred variations of the invention which can be used regardless of the Si/Al ratio of the catalyst, to limit the regeneration ratio of the catalyst so that the ratio of the amount of carbonaceous deposit on the removed (used) catalyst to the amount of carbonaceous deposit on the regenerated catalyst is relatively low, for example in the range 1.1 to 10, preferably in the range 1.2 to 6. The most preferred ratios are in the range 1.2 to 4 or in the range 1.3 to 3, or even in the range 1.3 to 2.5. This means that the catalytic activities of the used and regenerated catalyst are not too different, as that would greatly increase the hydrogen transfer and olefin saturation. This limitation to regeneration may be readily obtained by adjusting (reducing) the flow rate of the oxidizing gas, and/or the oxidation temperature and/or the partial pressure of oxygen. The rate of extracting the used catalyst may also be controlled or the residence time of the catalyst in the moving bed may be adjusted, in particular within the ranges cited above.

Normally, the catalytic cracking step is operated at a temperature of about 450° C. to about 650° C., preferably in the range 480° C. to 620° C., with a space velocity generally in the range 7 to 80 h$^{-1}$, in particular in the range 13 to 80 h$^{-1}$, or even in the range 33 to 60 h$^{-1}$. The operating pressure is generally in the range 0.1 to 5 MPa, usually in the range 0.1 to 1.5 MPa, and preferably in the range 0.1 to 0.5 MPa.

The conditions for regenerating the cracking catalyst generally employ a temperature in the range 300° C. to 900° C., in particular in the range 500° C. to 750° C., the pressure usually being close to the cracking pressure, or even close to atmospheric pressure.

In general, the propylene yield with respect to the quantity of olefins contained in the fresh feed for the process is in the range 30% to 60% by weight, usually in the range 40% to 60% by weight.

The process of the invention is not limited to the elements described above, and may be carried out in accordance with variations or with implementations not described in the present description but which are already known to the skilled person.

The invention claimed is:

1. A process for direct conversion, by catalytic cracking, of a light olefinic hydrocarbon feed comprising at least 80% by weight of hydrocarbons containing at most 12 carbon atoms for the production of propylene, said process comprising direct cracking of the feed on a supported catalyst comprising at least one zeolite comprising silicon and aluminum and having form selectivity, from the group constituted by zeolites with one of the following structure types: MEL, MFI, NES, EUO, FER, CHA, MFS, MWW, and from the following zeolites: NU-85, NU-86, NU-88 and IM-5, comprising circulating the feed at a temperature in the range about 480° C. to 620° C. in at least one reactor on a granular moving bed of said catalyst, extracting from the lower portion of the reactor, continuously or discontinuously, a flow of catalyst comprising a carbonaceous deposit, transferring said catalyst to a regeneration zone where it undergoes at least one controlled oxidation step, then downstream of the regeneration zone, re-introducing the catalyst comprising a reduced amount of carbonaceous deposit directly or indirectly into the upper portion of said reactor, the catalyst used being such that the zeolites from said group have a Si/Al ratio in the range 40 to 130 and in which the residence time for the catalyst in the reaction zone is in the range of 1 to 40 hours.

2. A process according to claim 1, in which at least 80% by weight of the feed is derived directly from one or more hydrocarbon cracking units.

3. A process according to claim 1, in which at least 10% by weight of the feed is derived directly from one or more Fischer-Tropsch synthesis units.

4. A process according to claim 1, in which the zeolite or zeolites of said group belong to the sub-group constituted by zeolites of structure type MEL, MFI and CHA.

5. A process according to claim 1, in which the zeolite or zeolites of said group are of structure type MFI.

6. A process according to claim 1, in which the zeolite or zeolites of said group are constituted by ZSM-5 zeolite.

7. A process according to claim 1, in which the overall space velocity HSV is in the range 13 to $80h^{-1}$.

8. A process according to claim 1, in which the overall space velocity is in the range 33 to $60h^{-1}$.

9. A process according to claim 1, in which the residence time for the catalyst in the reaction zone is in the range 2 to 18 hours.

10. A process according to claim 1, in which the overall space velocity HSV is in the range 13 to $80h^{-1}$.

11. A process according to claim 9, in which the overall space velocity HSV is in the range 13 to $80h^{-1}$.

12. A process according to claim 1, in which the overall space velocity is in the range 33 to $60h^{-1}$.

13. A process according to claim 9, in which the overall space velocity is in the range 33 to $60h^{-1}$.

14. A process according to claim 1, wherein said granular moving bed comprises beads or extrudates having a diameter in the range of 0.6 to 4 mm.

15. A process according to claim 14, wherein said granular moving bed comprises beads or extrutates having a diameter in the range of 0.4 to 6 mm.

16. A process for direct conversion, by catalytic cracking, of a light olefinic hydrocarbon feed comprising at least 80% by weight of hydrocarbons containing at most 12 carbon atoms for the production of propylene, said process comprising direct cracking of the feed on a supported catalyst comprising at least one zeolite comprising silicon and aluminum and having form selectivity, from the group constituted by zeolites with one of the following structure types: MEL, MFI, NES, EUO, FER, CHA, MFS, MWW, and from the following zeolites: NU-85, NU-86, NU-88 and IM-5, consisting of circulating the feed at a temperature in the range about 480° C. to 620° C. in at least one reactor on a granular moving bed of said catalyst, extracting from the lower portion of the reactor, continuously or discontinuously, a flow of catalyst comprising a carbonaceous deposit, transferring said catalyst to a regeneration zone where it undergoes at least one controlled oxidation step, then downstream of the regeneration zone, re-introducing the catalyst comprising a reduced amount of carbonaceous deposit directly or indirectly into the upper portion of said reactor, the catalyst used being such that the zeolites from said group have a Si/Al ratio in the range 40 to 130 and in which the residence time for the catalyst in the reaction zone is in the range of 1 to 40 hours.

* * * * *